(12) United States Patent
Rushbrooke et al.

(10) Patent No.: US 6,635,886 B1
(45) Date of Patent: Oct. 21, 2003

(54) BIOMEDICAL ASSAYS

(75) Inventors: John Gordon Rushbrooke, Cambridge (GB); Claire Elizabeth Hooper, Cambridge (GB); John David Tomisek, Lombard, IL (US)

(73) Assignee: Packard Instrument Company, Inc., Meridan, CT (US)

( * ) Notice: Subject to any disclaimer, the term of this patent is extended or adjusted under 35 U.S.C. 154(b) by 0 days.

(21) Appl. No.: 09/646,775

(22) PCT Filed: Mar. 18, 1999

(86) PCT No.: PCT/GB99/00828
§ 371 (c)(1),
(2), (4) Date: Nov. 22, 2000

(87) PCT Pub. No.: WO99/50648
PCT Pub. Date: Oct. 7, 1999

(30) Foreign Application Priority Data

Mar. 30, 1998 (GB) .............................................. 9806752
Apr. 2, 1998 (GB) .............................................. 9807061

(51) Int. Cl.⁷ .............................................. G01N 21/64
(52) U.S. Cl. .............................. 250/458.1; 250/459.1; 250/461.1
(58) Field of Search .......................... 250/458.1, 459.1, 250/461.1

(56) References Cited

U.S. PATENT DOCUMENTS

| 4,100,416 | A |   | 7/1978  | Hirschfeld | 250/416 B |
| 5,040,889 | A | * | 8/1991  | Keane      | 250/461.1 |
| 5,074,306 | A |   | 12/1991 | Green      | 128/664   |
| 5,111,821 | A |   | 5/1992  | Potter     | 128/654   |
| 5,387,527 | A |   | 2/1995  | Sternberg  | 436/518   |

FOREIGN PATENT DOCUMENTS

| EP | 0 737 855 | 10/1996 |
| GB | 2 043 876 | 10/1980 |
| JP | 7043303   | 2/1995  |

* cited by examiner

*Primary Examiner*—Constantine Hannaher
*Assistant Examiner*—Timothy Moran
(74) *Attorney, Agent, or Firm*—Barnes & Thornburg (57) ABSTRACT

Method of performing a biomedical assay comprising the steps of exciting the sample or samples with incident radiation of a given wavelength, thereby causing the sample to emit radiation of a different wavelength, measuring the quantity of light falling on a detector receiving the emitted radiation from the sample, thereby to produce a first measurement, illuminating the sample or samples with incident radiation in a manner which does not cause the sample to emit any significant radiation, again detecting the quantity of light falling on the detector, thereby to produce a second measurement and correcting the first measurement, with respect to the second measurement.

31 Claims, 5 Drawing Sheets

E = excitation light
B = background light from reflections
S = signal light from fluorescence in sample

BIOMEDICAL ASSAYS

FIELD OF THE INVENTION

This invention concerns biomedical assays in which light is emitted by a light emitting component (if present), usually triggered by excitation.

BACKGROUND

In such assays, the existence of the light emitting component is determined by detecting the emitted light using a sensitive light detecting device such as a cooled CCD detector or the like.

The wavelength of the emitted light is unique to the component and by using filters etc. the presence of other wavelengths can theoretically be masked from the detector. However, for various reasons, significant quantities of light at other wavelengths can reach the detector, during the light detection mode.

Thus, in assay systems in which a sample or samples are emitting light, the minimal detectable light signal is governed by the light arising from various sources of background in the assay matrix and detection system. Accurate and precise measurement of background as well as of signal is a crucial step in determining the sensitivity of the assay. Such assay detection methods include fluorescence by epi- and trans-illumination; luminescence, including chemi- and bio-luminescence; and radioisotopic methods.

Variations in the efficiency of detection of light from such assays, particularly resulting from uncertainty in the position of the sample or samples with respect to the detector input, from lateral or vertical displacements and from angular displacement or orientation, also contribute to errors in measurement.

Again, scatter and reflections of excitation light from the sample matrix make a significant contribution to background in the detection system, and hence to the uncertainty of error in the measurement of background.

Typical matrices for sample presentation include the following: a multi-well plate (e.g. a microplate); a dish or tray; a membrane; a gel; a glass or silicon wafer type presentation substrate; a cuvette or a capillary or an array of such. Variations in the sample presentation matrix itself which can give rise to detection errors include non-flatness, curvature, ripples or dimples, undulations, variations in the thickness, transparency or reflectivity of the material of the matrix, any or all of which can modify the amount of light reaching the detector. Examples of this include the transparent base of a multi-well plate or dish, both across the plate as a whole and within the area of the well itself; membranes which can have undulations and thickness variations; and sample presentation substrates which can have variations in reflectivity.

OBJECT OF THE INVENTION

The present invention seeks to allow the contribution of the light received by the detector from these variable sources of background to be quantified on an assay by assay basis, thereby allowing greater statistical certainty to be placed on the output signals from the detector when the assay is illuminated with excitation wavelengths, in the detection mode.

THE INVENTION

According to one aspect of the present invention there is provided a method of performing a biomedical assay, comprising the steps of:

exciting the sample or samples with incident radiation of a given wavelength, thereby causing the sample to emit radiation of a different wavelength, measuring the quantity of light falling on a detector receiving the emitted radiation from the sample, thereby to produce a first measurement, illuminating the sample or samples with incident radiation in a manner which does not cause the sample or samples to emit any significant radiation, again detecting the quantity of light falling on the detector, thereby to produce a second measurement, and correcting the first measurement with respect to the second measurement.

The first and second measurements may be made in either order.

In a less preferred method, in order to produce the second measurement, a light emission inhibitor is added to the sample or samples, and the sample or samples are illuminated with the same wavelength of radiation used to excite the sample or samples in order to obtain the first measurement.

In a preferred method, in order to produce the second measurement, the sample or samples are illuminated with a wavelength of light selected not to give rise to any significant emission of light from the sample or samples. The light of selected wavelength may lie in the infra-red or the ultra-violet region.

According to another aspect of the invention, there is provided apparatus for performing a biomedical assay in which light is emitted from a sample or samples when excited by incident radiation, comprising:

means for illuminating the sample or samples with incident radiation of two differing wavelengths, detection means for detecting the radiation emitted by the sample when illuminated at the two wavelengths, thereby to produce a first and second measurement, and means for correcting one measurement with respect to the other measurement.

DESCRIPTION OF DRAWINGS

The invention is further described with reference to the accompanying drawings, in which.

DESCRIPTION OF EXAMPLES

Figure 1:
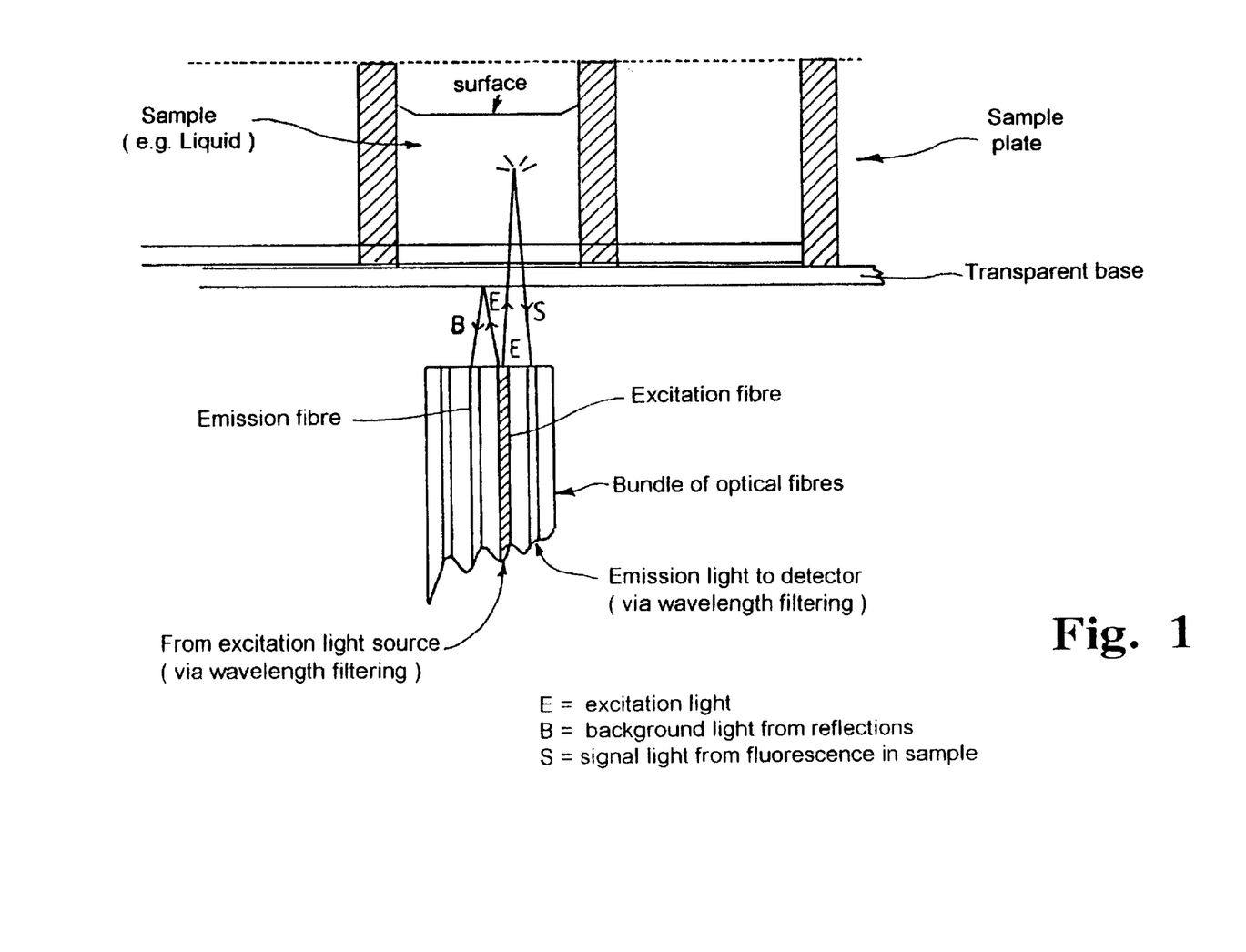
FIG. 1 shows the detector/sample interface of a single channel of a detection system for making epi-fluorescence measurements for a biomedical assay.

In FIG. 1 is shown a detector-sample interface of a single channel of a detection system for epi-fluorescence measurements. A reading head may employ a single detection channel or may employ multiple detection channels, e.g. 12 or 96 channels. A single well with a thin transparent base containing a sample (e.g. a solution of fluorophore or fluorescent labelled material such as cells) is situated above a single channel of the reading head which is designed both to illuminate the sample with excitation light and to receive the resultant fluorescence generated light. In the example shown the reading head comprises a bundle of optical fibres, which are a mixture of excitation and emission fibres. The excitation fibres convey wavelength-specific excitation light to the sample; the uniformity and efficiency of illumination are determined by the pattern of fibres, their numerical aperture and their distance from and registration with the base of the sample well. The efficiency of the emission fibres in gathering light from the well depends in a similar manner on these properties. The emission light is subsequently wavelength selected (at one or more wavelengths) using filters and passed to the detector.

In FIG. 1 two excitation light rays labelled E are shown. One of these produces a fluorescence event upon interaction with a fluorophore at any point in the sample volume, which results in a signal light ray which can be emitted in all directions. In the example shown the signal ray S is received by an emission fibre of the reading head. The other excitation light ray undergoes reflection at the air/well base interface and is shown as being received as ray B by an emission fibre and is therefore a potential source of background light. Clearly a light ray E can strike any interface involving a change of refractive index, for example at the base of the plate or at the liquid/air interface at the top of the sample, and be reflected back into the detector.

Excitation light entering the emission fibres can be accepted by the detector in a variety of ways. Thus, even though the excitation light has a different wavelength (generally shorter) than the signal light generated from the fluorophore, such light rays can pass straight through the emission filters (typically interference or other band pass filters). This occurs because of overlap of transmission wavelengths between excitation and emission filters (especially in the case of short Stokes shift) and the intense excitation light can exceed the blocking capability of the emission filters and result in measurable background signal. For example in the detection of fluorescein fluorescence, the excitation and emission wavelengths are typically 485 nm and 530 nm respectively. A further mechanism for excitation light to result in measurable background is the occurrence of large angle rays (e.g. skew rays) being transmitted by the optical fibres in the system, such that these rays are passed by the emission filter. It follows that excitation light captured by the emission fibres can pass through an emission interference filter (e.g. typically of effective refractive index 2) when the rays exit an emission fibre in a cone of half-angle of about 54 degrees which satisfies the transmission condition of the interference filter.

A further source of background in this fluorescence type assay can result from fluorescence of materials other than the specific signal fluorophore, for example from the plate and the plate base, or materials used in the sample presentation matrix; from the sample medium (e.g. from proteins and other materials in the case of immunoassays and cell-based assays); and all components of the detection system itself, including the optical components such as filters, optical fibres, adhesives and other materials.

Background produced by reflected light and detected, as described above, can be the dominant source of overall background in such epifluorescence assays. The variation and hence uncertainty in this background can therefore be a determining factor in the ultimate sensitivity and reproducibility of the assay. Other factors which can contribute to this variability include: scatter or reflections of the excitation light from the sample and the sample matrix which depend on sample matrix geometry; reflections from interfaces involving change in refractive index of medium; curvature or deformations of the sample presentation matrix, e.g. non-flatness of the sample plate and individual well bases which change the angular presentation and the stand-off of the sample from the reading head; errors in sample plate positioning over the reading head, both laterally (x. y) and vertically (z); variations in the transparency of the sample and the sample matrix, e.g. the well base; variations in the optics, geometry, positioning and efficiency of channels, including channel to channel variations within the reading head.

An example of a sample presentation format is a single or multi-well dish or plate, e.g. a nucroplate having an array of 96 (or multiples of 96 such as 384, 864, 1536, 2400, 3456, etc.) wells. A sample plate may contain liquid samples such as a solution of a fluorophore, an immunoassay complex, microparticles, or a suspension or monolayers of cells. Such a sample plate can be measured with the detection head either from above or from below the sample.

Figure 2A:
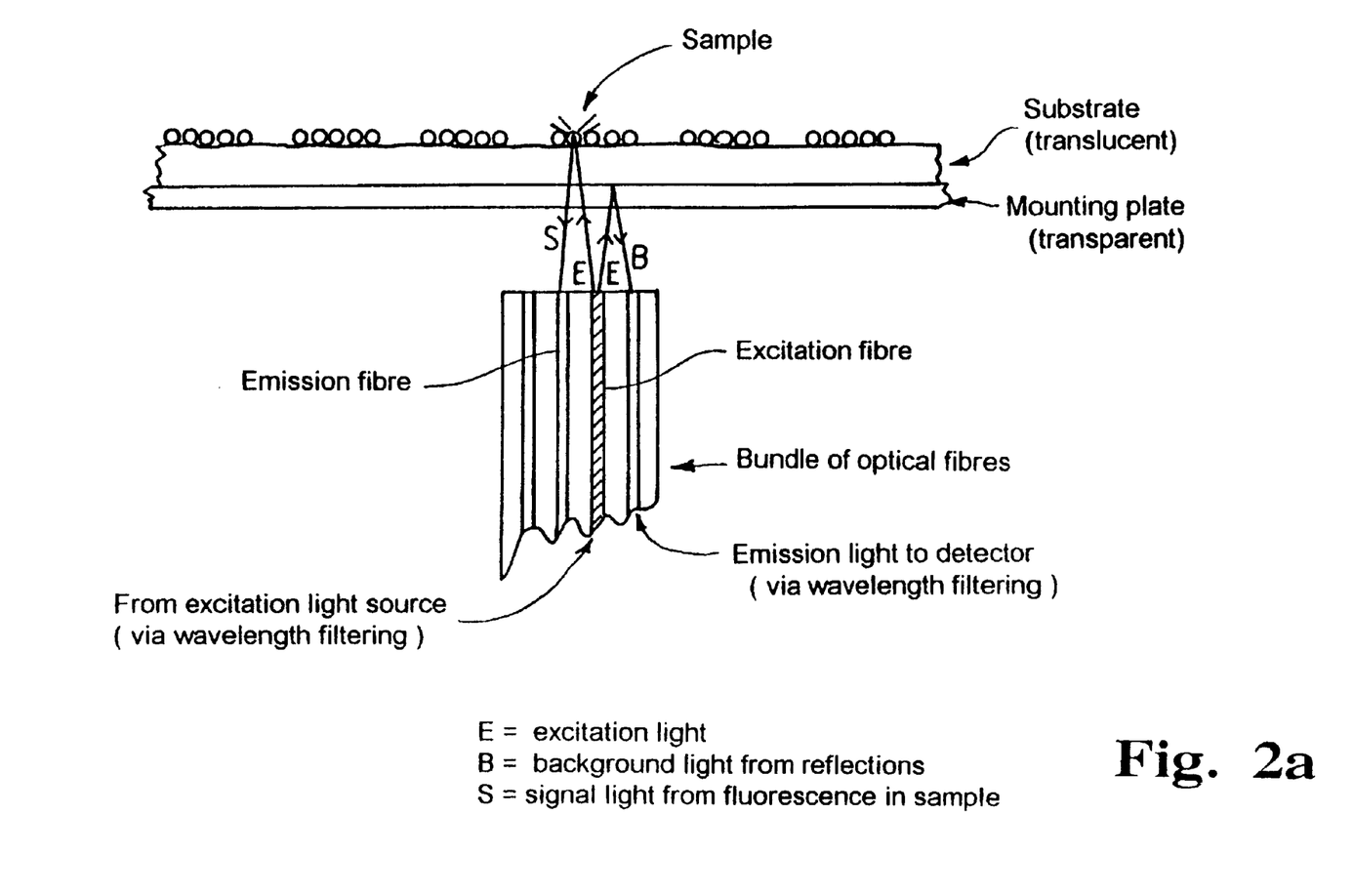
FIGS. 2A and 2B show the options of reading a gel array or membrane from below and above, respectively.
Figure 2B:
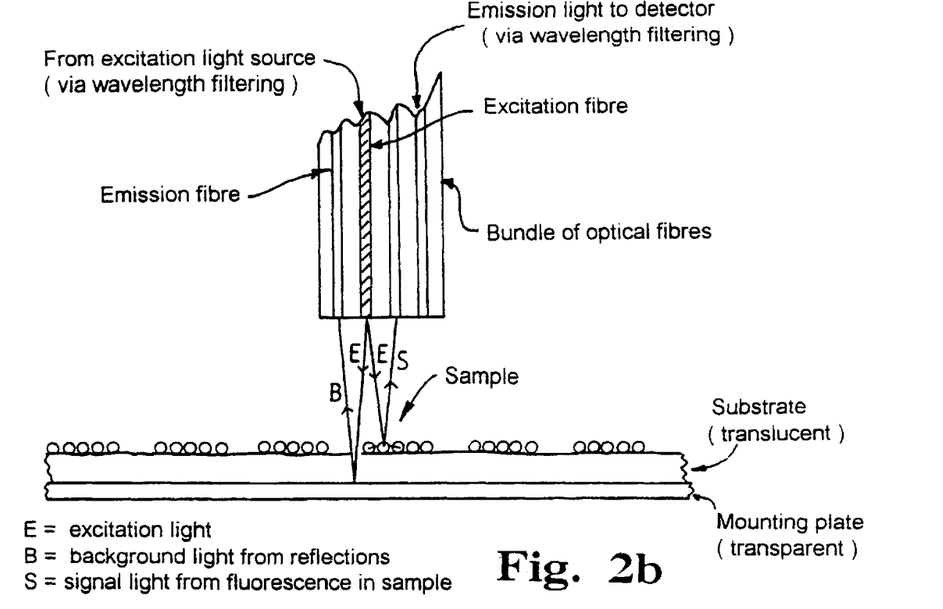

A further example of a sample presentation is a membrane or gel containing, either within the matrix or its surface, an array of biological samples, e.g. DNA or proteins. Such a matrix is typically translucent and may be mounted on a solid support such as a glass plate. Again, this sample presentation may be measured from above or below, depending on the type of sample and the transparency of the matrix. FIGS. 2(*a*) and (*b*) show the case of reading a gel array or membrane from below and above respectively.

Correction Procedures

Consider the case where a 96-channel reading head can measure simultaneously 96 wells of a sample plate, and wells of plates of higher multiples of 96 are read sequentially following lateral movements of the plate with respect to the reading head. For example a 1536 plate is read in 16 movements.

The first stage is to take out variations common to a given type of sample presentation matrix, in this example a multi-well plate. For example a typical 96- or 384-well microplate typically has a downwards convex curvature of the base with magnitude corresponding to 150–300 micron displacement normal to the base between the centre and edge of the plate, which results in variation in the stand-off of wells with respect to their corresponding reading head. A suitable procedure is to take, e.g., 12 plates of the given type containing fluorophore sample and 12 containing sample medium such as buffer solution (buffer blank), each well containing the same voume of material. In the case of cells the corresponding signal samples and background media would be used. The signal from each well of each plate is then measured. The number of plates to be used is chosen to give a statistically significant result for the purpose of correction.

Figure 3:
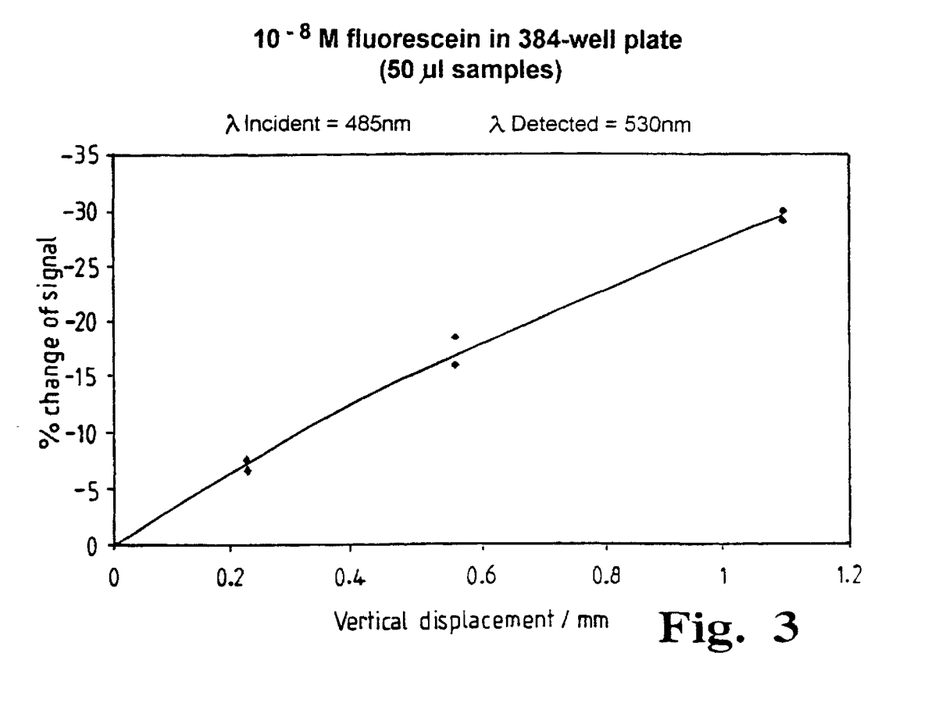
FIGS. 3 and 4 are graphs showing plots of incident radiation against emitted radiation respectively for a fluorescein sample and a buffer blank sample.
Figure 4:
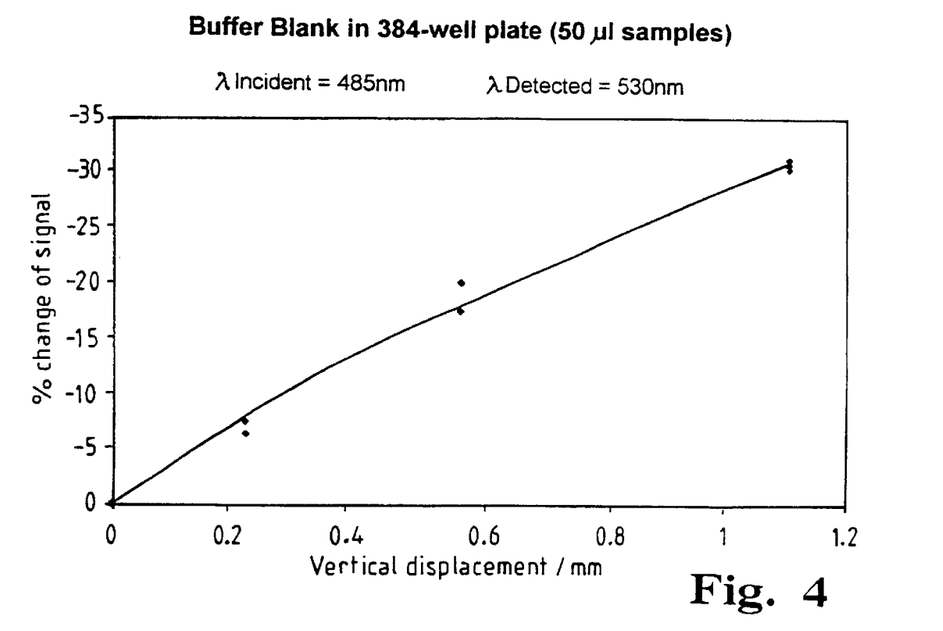

For the 12 plates containing fluorophore sample, the average measured signal across the wells is derived and a correction factor for each well and reading channel combination is calculated to bring the measured value back to the average. The same procedure is then followed for the next 12 plates containing buffer blank. This will allow one to correct for gross characteristics pertaining to the type of plate chosen and to correct for channel to channel efficiency variations in the instrument. For example the 150–300 micron plate stand-off may have resulted in a percentage loss of measured signal of as much as 10% compared to zero stand-off. FIGS. 3 and 4 show typical calibration curves, obtained in this example for $10^{-8}$ molar fluorescein and buffer blank respectively, measured using 50 microliter samples in 384-well clear base plates, plotted as the percentage loss of signal against the vertical displacement. This procedure reduces assay errors for signal and background to approximately 2–4% for multiple reading of different wells within the given type of plate, but leaves residual errors of this magnitude due to variations for a given well position from plate to plate, and errors within a given well positiion (e.g. flatness, dimpling or curvature of the well base which could amount to displacements of magnitude 25–75 microns, variations in sample meniscus, scratches and other defects).

The effect of mechanical positioning errors in the loading and placement of plates with respect to the reading head can also be assessed. This comprises repeatedly loading and reading a given plate, e.g. 12 times, and observing the spread of results measured from this process in order to derive an error. This procedure can be repeated with different plates, which will also give an indication of sample delivery or pipetting errors. This makes it possible to determine the magnitude of these types of error with respect to sample matrix and channel errors described above.

Some of the above-mentioned variations or errors will be systematic and hence recurring and can be allowed for by determining a correction factor for each well/channel combination.

A further stage of correction is designed to minimise the residual errors decribed above, which will be dominated by random effects for a given well as between different plates. It will be recalled that these result from small variations (e.g. 2–4%) in the sample and presentation matrix including variations in flatness of a well (especially dimples or bowing, and deformations of the thin well base caused by wetting by the sample), scratches, and meniscus variations, and pipetting errors which change the volumes or amounts of sample material delivered to each well to vary. For a given assay, a plate is loaded with unknown samples, containing unknown amounts of fluorophore in a pre-determined volume. The sensitivity and precision of the assay is now determined by the magnitude of these residual errors and variations, mainly as they affect buffer blank. This is because it is the uncertainty in buffer blank which determines the minimum detectable signal of the assay. It is normal practice to state the minimal detectable level of an assay as the concentration of the fluorophore or label which gives a signal of magnitude equal to 4 times the standard deviation on the buffer blank signal.

The correction procedure to minimise these residual uncertainties on background and signal, which are largely due to effects which change stand-off or displacement between a given well and the reading head, depends on being able to monitor or sense this effect with some quantitative probe, with the sample plate mounted in situ on the reading head. The use of a mechanical or laser probe to sense the stand-off variation could be envisaged, but is limited by the restricted access to the sample in some cases, and is therefore impractical in general.

A further correction procedure with which the present invention is especially concerned therefore involves using a second wavelength range or ranges to illuminate and detect light from the samples being measured, so chosen to be off the peak wavelengths relevant to a given sample fluorophore being measured, so that it does not induce significant secondary fluorescence in the sample. This is achieved by appropriate choice of excitation and emission filters, outside the wavelength range of the assay. This procedure utilises the existing excitation and emission light paths in the detector, and by so doing the optical paths of illumination and light gathering are the same as for the specific assay sample measurement. The signals measured for each well will therefore represent the relative magnitude of the variations for each well, and hence can be used to derive correction factors, bringing each well into an average value. Thus, for example, buffer blank which as described above can be dominated by reflections from the well base and meniscus (which vary from well to well and plate to plate) will be mimicked by the measurement at the second wavelength. In particular the influence of skew rays and their ability to penetrate the emission interference filter will be reproduced by choosing a ratio of excitation radiation wavelength to emission radiation wavelength similar to that of the actual assay. For example the specific values for fluorescein are 485/530 nm and the correction procedure may use wavelength 780/830 nm.

As stated, FIG. 4 shows a plot of loss signal with stand-off or displacement when the buffer blank sample is excited with 485 nm light, i.e. the sample excitation wavelength, and emitted radiation is detected at 530 nm.

Figure 5:
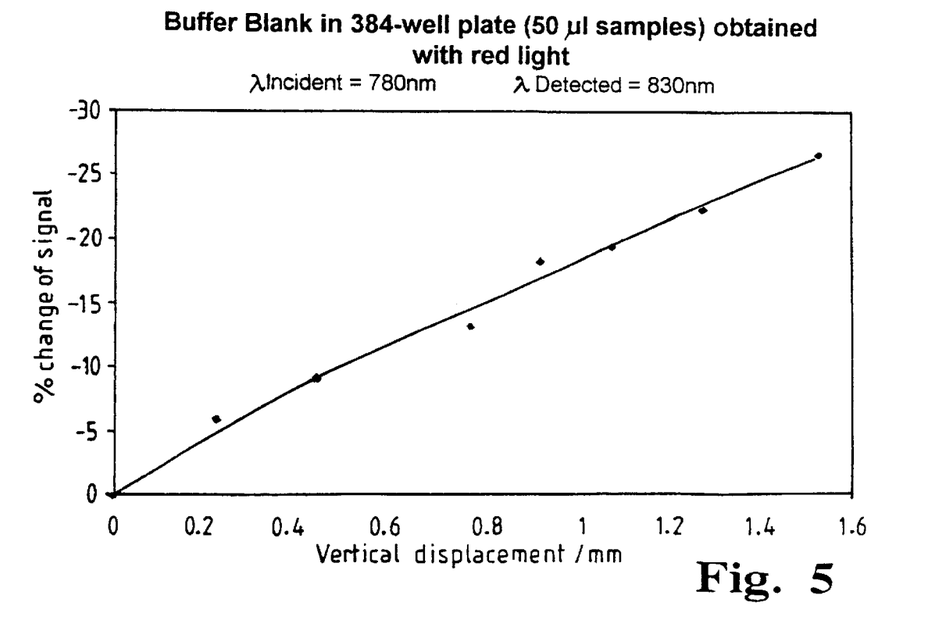
FIGS. 5 to 7 are graphs respectively showing plots of incident radiation against emitted radiation for a buffer blank sample illuminated with wavelengths producing no significant fluorescence from the sample.

In FIG. 5 is shown a plot equivalent to that of FIG. 4, obtained as an example with red light (780/830 nm). It can be seen that the same type of dependency of loss of signal with stand-off or displacement is obtained in the red as was obtained with the specific blue/green wavelength combination of FIG. 4. This procedure also senses changes in sample volume in proportion with the specific wavelength. This demonstrates that relative correction factors, as between wells, can be obtained using light in a different wavelength band from that needed for the assay.

Although UV as well as red light could have been chosen in this example, the UV excitation would most likely result in non-specific fluorescence from the sample and matrix and hence be unsuitable. The wavelengths selected for this correction procedure should however, in any case, be within the detection range or quantum efficiency of the detector being employed. The example given here utilises a cooled CCD, which has relatively high quantum efficiency in the red (30–40%) and even towards the IR, as compared to the blue/green range (5–15%). Wavelength ranges even up to approximately 1000 nm could therefore be used for this procedure, provided the optical detection system can pass these wavelengths.

Figure 6:
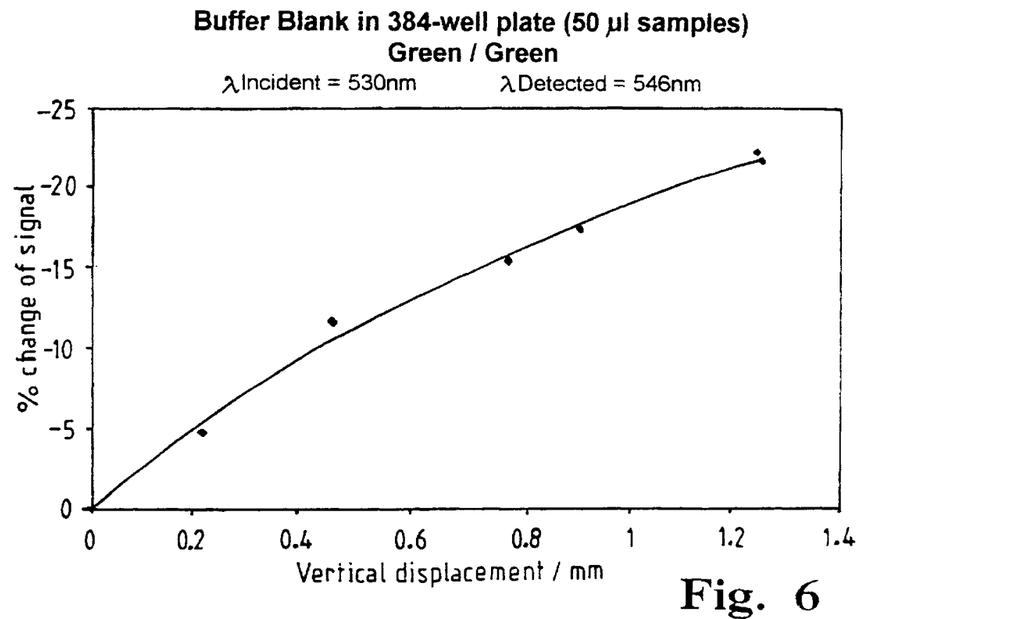

Thus, one further example uses wavelengths in the green, such as 530/546, for which experimental data is shown in FIG. 6.

Figure 7:
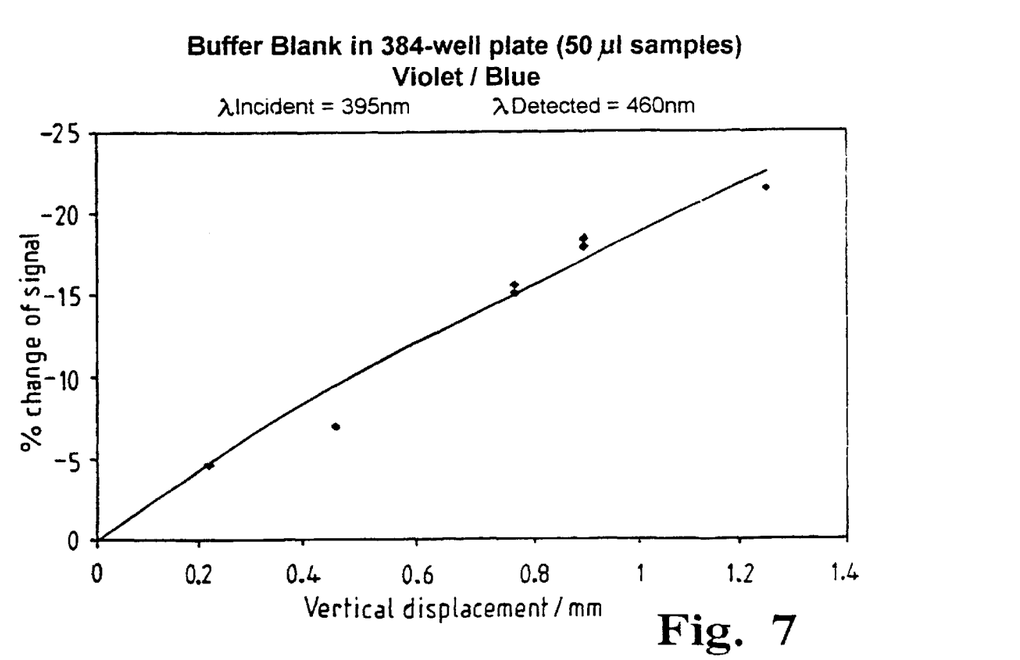

A still further example uses violet/blue light, such as 395/460 nm, for which experimental data is shown in FIG. 7.

Further wavelength combinations, such as green/yellow or yellow/red may be used.

Clearly an appropriate choice must be made for each plate, detector, buffer assay, sample combination under investigation, where, as already stated, the sample can contain fluorescent, chemiluminescent or bioluminescent labels or markers or dyes, or be a radioisotopic sample.

The invention disclosed herein allows the error signals (equivalent to noise) generated in the detector inter alia by assay-plate imperfections and from the mere presence of buffer solution in the plate-wells, to be isolated from signals generated inter alia from light emission from the assay sample material, triggered by incident excitation wavelengths.

Previous attempts to achieve this, by using the same plate with the same buffer solution in the absence of any sample material have failed. This is due to the large variation in the signal caused by variations in meniscus height, random presence of suspended particles, changes in well wetting angle, and others, quite apart from registration inaccuracies of the plate if moved and relocated in position. Whilst variations in the components due to these effects are substantially eliminated when an assay plate is left in place and no attempt is made to change the contents of the wells, all of these variables mitigate against a satisfactory determination of the background signal (or an assessment of errors attributable to changes in the background signal) if it is necessary to remove the plate, wash it, refill with buffer, and relocate, before a check on the signals emanating from the plate in the absence of assay sample material can be performed.

The invention thus provides a technique for error signal determination which does not entail any changes being made to the liquid content of the wells, nor movement, nor cleaning of, the plate. This is achieved by changing the wavelength of the incident light for a calibration measurement so that little or no light emission from the assay sample material is triggered, and any light received by the detector can only arise from reflection, refraction, and imperfections etc. in the plate and/or buffer liquid in the plate/well(s) under test. This can be used to correct both detected signals from light emitting assay sample material as well as background signals (i.e. detector output when no light emission from assay sample material is occurring).

The calibration measurement may be performed before or after the assay is illuminated with excitation wavelength light, to allow the assay assessment to be made.

Since contributions to the background signal arising from some of the aforementioned variables can appear as 1–2% variation in the background signal contribution, which can therefore mask or equate to small light level changes due to triggered light emission from sample material if present, it will be seen that the invention allows a very significant improvement in signal to noise level discrimination to be obtained, when detecting emitted light from low-light-level emitting assays, and for very low-light-level emitting assays to be monitored and much greater statistical certainty to be attributed to the light detector output.

In the case of a cellular monolayer, e.g. at the base of a well, small variations in stand-off affect signal and background and would need to be corrected for in the above described manner to reduce errors.

The examples given in FIGS. 1, 2 and 3 show a single channel of a detector, but could clearly be generalised to include multiple channels such as 96 in the same reading system.

The light detector used to measure the light signals could be an imaging detector such as a charge coupled device (CCD), image intensifier or intensified CCD, or a single channel detector such as a photomultiplier tube (PMT) or photodiode.

As an alternative to the above method, a different technique can be used to inhibit fluorescence. This can be done by introducing a light emission inhibitor using the same incident and detected wavelengths as used for the fluorescence examination of the sample, by first introducing a chemical reagent either in liquid or gaseous form, into the or each well, which has the effect of extinguishing or quenching or masking any light emission which would otherwise be emitted from the sample, in the presence of or following excitation wavelengths.

In the case of radioisotope and/or chemiluminecent type assays, a similar approach may be employed, using a suitable additive to extinguish mask or otherwise remove the light emission which is otherwise occurring.

What is claimed is:

1. A method of performing a biomedical assay in which light is emitted by a sample or samples when excited by incident radiation in order to obtain an error corrected measurement signal, comprising the steps of:
   exciting the sample or samples along an excitation path with incident radiation of a given wavelength, thereby causing the sample to emit radiation of another wavelength transmitted along an emission path,
   measuring the quantity of light falling on a detector receiving the emitted radiation from the sample along the emission path, thereby to produce a first measurement,
   at a different time illuminating the sample or samples along the same excitation path with incident radiation of a different wavelength which does not cause the sample or samples to emit any significant radiation,
   detecting the quantity of light transmitted along the same emission path to fall on the same detector, thereby to produce a second measurement, and
   correcting the first measurement with respect to the second measurement, whereby to correct the first measurement in respect of errors, including errors inherent in the measurement system.

2. A method according to claim 1, wherein the detector is a charge coupled device (CCD), an image intensifier, an intensified CCD, a cooled CCD, or a single channel detector.

3. A method according to claim 2, wherein the different wavelength for obtaining the second measurement is higher than the excitation wavelength for the first measurement whilst remaining within the detection range and/or quantum efficiency of the detector.

4. A method according to claim 1, wherein the different wavelength for the second measurement is 780 nm giving rise to substantially no emitted radiation from the sample or samples and detected at 830 nm.

5. A method according to claim 1, wherein the different wavelength for the second measurement is 530 nm giving rise to substantially no emitted radiation from the sample or samples and detected at 546 nm.

6. A method according to claim 1, wherein the different wavelength for the second measurement is 395 nm giving rise to substantially no emitted radiation from the sample or samples and detected at 460 nm.

7. A method according to claim 1, wherein the first measurement is also corrected for mechanical positioning errors in the positioning of samples with respect to a reading head by reading the sample a plurality of times and deriving an error signal from the spread of resulting measurements.

8. Apparatus for performing a biomedical assay in which light is emitted from a sample or samples when excited by incident radiation, comprising:
   means operative at different times respectively for illuminating the sample or samples along the same excitation path with incident radiation of two differing wavelengths, one of which does not cause the sample to emit any significant radiation,
   a detector for detecting the radiation emitted by the sample when illuminated at the two wavelengths, thereby to produce first and second measurements from the same detector, and
   means for correcting one measurement with respect to the other measurement.

9. Apparatus according to claim 8, wherein the radiation incident on the sample or samples and the radiation emitted from the sample or samples is conveyed by a reading head having at least one channel comprising a bundle of optical fibres which are a mixture of fibres for illumination light with fibres for receiving radiation to be detected.

10. Apparatus according to claim 8, wherein the detecting means is a charge coupled device (CCD), an image intensifier, an intensified CCD, a cooled CCD, or a single channel detector.

11. A method of performing a biomedical assay in which light is emitted by a sample or samples when excited by incident radiation in order to obtain an error corrected measurement signal, comprising the steps of:

exciting the sample or samples along an excitation path with incident radiation of a given wavelength, thereby causing the sample to emit radiation of another wavelength transmitted along an emission path, measuring the quantity of light falling on a detector receiving the emitted radiation from the sample along the emission path, thereby to produce a first measurement, at a different time illuminating the sample or samples along the same excitation path with incident radiation of a different wavelength which does not cause the sample or samples to emit any significant radiation, wherein the light of different wavelength lies in the infra-red region, detecting the quantity of light transmitted along the same emission path to fall on the same detector, thereby to produce a second measurement, and correcting the first measurement with respect to the second measurement, whereby to correct the first measurement in respect of errors, including errors inherent in the measurement system.

12. A method according to claim 11, wherein the detector is a charge coupled device (CCD), an image intensifier, an intensified CCD, a cooled CCD, or a single channel detector.

13. A method according to claim 12, wherein the different wavelength for obtaining the second measurement is higher than the excitation wavelength for the first measurement whilst remaining within the detection range and/or quantum efficiency of the detector.

14. A method according to claim 11, wherein the different wavelength for the second measurement is 780 nm giving rise to substantially no emitted radiation from the sample or samples and detected at 830 nm.

15. A method according to claim 11, wherein the different wavelength for the second measurement is 530 nm giving rise to substantially no emitted radiation from the sample or samples and detected at 546 nm.

16. A method according to claim 11, wherein the different wavelength for the second measurement is 395 nm giving rise to substantially no emitted radiation from the sample or samples and detected at 460 nm.

17. A method according to claim 11, wherein the first measurement is also corrected for mechanical positioning errors in the positioning of samples with respect to a reading head by reading the sample a plurality of times and deriving an error signal from the spread of resulting measurements.

18. A method of performing a biomedical assay in which light is emitted by a sample or samples when excited by incident radiation in order to obtain an error corrected measurement signal, comprising the steps of:

exciting the sample or samples along an excitation path with incident radiation of a given wavelength, thereby causing the sample to emit radiation of another wavelength transmitted along an emission path, measuring the quantity of light falling on a detector receiving the emitted radiation from the sample along the emission path, thereby to produce a first measurement, at a different time illuminating the sample or samples along the same excitation path with incident radiation of a different wavelength which does not cause the sample or samples to emit any significant radiation, wherein the light of different wavelength lies in the ultraviolet region, detecting the quantity of light transmitted along the same emission path to fall on the same detector, thereby to produce a second measurement, and correcting the first measurement with respect to the second measurement, whereby to correct the first measurement in respect of errors, including errors inherent in the measurement system.

19. A method according to claim 18, wherein the detector is a charge coupled device (CCD), an image intensifier, an intensified CCD, a cooled CCD, or a single channel detector.

20. A method according to claim 19, wherein the different wavelength for obtaining the second measurement is higher than the excitation wavelength for the first measurement whilst remaining within the detection range and/or quantum efficiency of the detector.

21. A method according to claim 18, wherein the different wavelength for the second measurement is 780 nm giving rise to substantially no emitted radiation from the sample or samples and detected at 830 nm.

22. A method according to claim 18, wherein the different wavelength for the second measurement is 530 nm giving rise to substantially no emitted radiation from the sample or samples and detected at 546 nm.

23. A method according to claim 18, wherein the different wavelength for the second measurement is 395 nm giving rise to substantially no emitted radiation from the sample or samples and detected at 460 nm.

24. A method according to claim 18, wherein the first measurement is also corrected for mechanical positioning errors in the positioning of samples with respect to a reading head by reading the sample a plurality of times and deriving an error signal from the spread of resulting measurements.

25. A method of performing a biomedical assay in which light is emitted by a sample or samples when excited by incident radiation in order to obtain an error corrected measurement signal, comprising the steps of:

exciting the sample or samples along an excitation path with incident radiation of a given wavelength, thereby causing the sample to emit radiation of another wavelength transmitted along an emission path, measuring the quantity of light falling on a detector receiving the emitted radiation from the sample along the emission path, thereby to produce a first measurement, at a different time illuminating the sample or samples along the same excitation path with incident radiation of a different wavelength which does not cause the sample or samples to emit any significant radiation, detecting the quantity of light transmitted along the same emission path to fall on the same detector, thereby to produce a second measurement, correcting the first measurement with respect to the second measurement, whereby to correct the first measurement in respect of errors, including errors inherent in the measurement system, and wherein, when a multiple channel reading head reading a multiplicity of samples is employed, the first measurement is also corrected for variation in the stand-off of samples with respect to the reading head by averaging the first measurement over a plurality of the said multiplicity of samples.

26. A method according to claim 25, wherein the detector is a charge coupled device (CCD), an image intensifier, an intensified CCD, a cooled CCD, or a single channel detector.

27. A method according to claim 26, wherein the different wavelength for obtaining the second measurement is higher than the excitation wavelength for the first measurement whilst remaining within the detection range and/or quantum efficiency of the detector.

28. A method according to claim 25, wherein the different wavelength for the second measurement is 780 nm giving rise to substantially no emitted radiation from the sample or samples and detected at 830 nm.

29. A method according to claim 25, wherein the different wavelength for the second measurement is 530 nm giving rise to substantially no emitted radiation from the sample or samples and detected at 546 nm.

30. A method according to claim 25, wherein the different wavelength for the second measurement is 395 nm giving rise to substantially no emitted radiation from the sample or samples and detected at 460 nm.

31. A method according to claim 25, wherein the first measurement is also corrected for mechanical positioning errors in the positioning of samples with respect to a reading head by reading the sample a plurality of times and deriving an error signal from the spread of resulting measurements.

* * * * *